(12) United States Patent
Miyamoto (10) Patent No.: US 8,821,531 B2
(45) Date of Patent: Sep. 2, 2014

(54) TREATMENT TOOL (71) Applicant: Olympus Medical Systems Corp., Tokyo (JP)

(72) Inventor: Manabu Miyamoto, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/866,653

(22) Filed: Apr. 19, 2013

(65) Prior Publication Data

US 2013/0304115 A1 Nov. 14, 2013

Related U.S. Application Data

(63) Continuation of application No. PCT/JP2012/069352, filed on Jul. 30, 2012.

(60) Provisional application No. 61/515,430, filed on Aug. 5, 2011.

(51) Int. Cl.
*A61B 17/00* (2006.01)
*A61B 19/00* (2006.01)
*A61B 17/29* (2006.01)
*A61B 17/28* (2006.01)

(52) U.S. Cl.
CPC ............ *A61B 17/2909* (2013.01); *A61B 19/00* (2013.01); *A61B 2017/2944* (2013.01); *A61B 2017/2936* (2013.01); *A61B 17/28* (2013.01)
USPC ........................................................ 606/205

(58) Field of Classification Search
CPC .............. A61B 2017/2946; A61B 2017/2905; A61B 17/122; A61B 17/2909; A61B 18/1445; A61B 17/28; A61B 17/2833

USPC ................... 606/51, 52, 167, 170, 171, 174, 606/205–208; 30/134, 186–196, 211, 30/272.1; 74/473.3; 600/214, 208
See application file for complete search history.

(56) References Cited

U.S. PATENT DOCUMENTS

2002/0165564 A1* 11/2002 Danitz et al. .................. 606/151

FOREIGN PATENT DOCUMENTS

| JP | A-6-296618 | 10/1994 |
|---|---|---|
| JP | A-8-71072 | 3/1996 |
| JP | A-2008-93271 | 4/2008 |

OTHER PUBLICATIONS

International Search Report issued in International Patent Application No. PCT/JP2012/069352 on Sep. 4, 2012 (with translation).

* cited by examiner

*Primary Examiner* — Katherine M Shi
(74) *Attorney, Agent, or Firm* — Oliff PLC (57) ABSTRACT

A treatment tool includes a long shaft member, a pair of grasping members installed at a distal end portion of the long shaft member, a driving force transmission member connected to the pair of grasping member, a driving manipulation member, and a switch unit having a first sliding section and a second sliding section, and configured to switch a ratio of a magnitude of a force for moving the driving force transmission member with respect to a magnitude of a force for moving the driving manipulation member when the driving manipulation member is manipulated to be moved by switching a position at which the driving manipulation member is slid between the first sliding section and the second sliding section.

4 Claims, 10 Drawing Sheets

TREATMENT TOOL

Priority is claimed on U.S. Provisional Application No. 61/515,430, filed Aug. 5, 2011, and the application is a continuation application of PCT/JP2012/069352, filed Jul. 30, 2012, both of which are incorporated herein by reference.

BACKGROUND OF THE INVENTION

1. Field of the Invention

The present invention relates to a treatment tool.

2. Background Art

In the related art, a treatment tool used with a flexible endoscope is configured to transmit a driving force from a manipulation unit to a treatment unit by a wire, a coil, or the like. Since the wire or the coil may be expanded or contracted by the driving force, such a treatment tool has a configuration of moving the wire or the coil to an extent larger than a necessary minimum movement amount corresponding to a movable range of the treatment unit.

Japanese Unexamined Patent Application, First Publication No. H06-296618 discloses a configuration of a manipulation unit configured to rotate a driving manipulation member (a movable handle) about a predetermined rotate point as a rotational center and move a manipulation rod by a driving manipulation member, which is rotated.

In the conventional treatment tool, a relation of a moving speed of the treatment unit to a moving speed of the driving manipulation unit or a relation between a force applied to the driving manipulation member by an operator and a force of operating the treatment unit keeps definite relation.

SUMMARY OF THE INVENTION

A treatment tool according to a first aspect of the present invention includes a long shaft member having a distal end portion and a proximal end portion, and a longitudinal axis extending from the distal end portion to the proximal end portion; a pair of grasping members installed at the distal end portion of the long shaft member so as to be freely opened and closed with each other to grasp a target area; a driving force transmission member connected to the pair of grasping members and movably extending along the longitudinal axis with respect to the long shaft member; a driving manipulation member connected to a proximal end portion of the driving force transmission member and configured to manipulate the driving force transmission member to be moved with respect to the long shaft member; and a switch unit having a first sliding section configured to support the driving manipulation member so as to be capable of sliding at a position at which a magnitude of a force for moving the driving force transmission member with respect to a magnitude of a force for moving the driving manipulation member becomes a first ratio when the driving manipulation member is manipulated to be moved, and a second sliding section configured to support the driving manipulation member so as to be capable of sliding at a position at which the magnitude of a force becomes a second ratio different from the first ratio, and the switch unit configured to switch the first ratio and the second ratio by switching a position at which the driving manipulation member is slid between the first sliding section and the second sliding section.

According to a treatment tool of a second aspect of the present invention, in the treatment tool according to the first aspect, the driving manipulation member may be movable with respect to a manipulation unit main body installed at the proximal end portion of the long shaft member. In addition, according to a manipulation amount of the driving manipulation member with respect to the manipulation unit main body, the switch unit may open and close the pair of grasping members and may switch a ratio of a movement amount of the driving force transmission member with respect to a manipulation amount of the driving manipulation member with respect to the manipulation unit main body. Further, the switch unit may switch a moving state of the driving manipulation member with respect to the manipulation unit main body into a moving state of any one of a first state in which the driving manipulation member is rotated about a first rotational center with respect to the manipulation unit main body and a second state in which the driving manipulation member is rotated about a second rotational center different from the first rotational center with respect to the manipulation unit main body.

According to a third aspect of the present invention, in the treatment tool according to the second aspect, the driving manipulation member may move from a start position to an end position or from the end position to the start position substantially in one direction with respect to the manipulation unit main body. The switch unit may switch a rotational center of the driving manipulation member with respect to the manipulation unit main body from the first rotational center to the second rotational center or from the second rotational center to the first rotational center at at least one location between the start position and the end position. Provided that a magnitude of a force applied to the driving manipulation member is set as $F_{in}$, a magnitude of a force of driving the driving force transmission member via the switch unit is set as $F_{out}$, a distance between an input section and the first rotational center when a predetermined point at which a force is applied to the driving manipulation member to manipulate the driving manipulation member is designated as the input section is set as $L_1$, a distance between a connecting position of the driving force transmission member to the driving manipulation member and the first rotational center is set as $L_2$, a distance between the input section and the second rotational center is set as $L_3$, and a distance between the connecting position and the second rotational center is set as $L_4$, a relational expression in the first state is $F_{out}/F_{in}=L_1/L_2$, a relational expression in the second state is $F_{out}/F_{in}=L_3/L_4$, and $L_1/L_2 < L_3/L_4$.

According to a fourth aspect of the present invention, in the treatment tool according to the first aspect, the first sliding section and the second sliding section may be formed continuously each other, when the driving manipulation member is disposed at the first sliding section, a ratio between the magnitude of the force applied to the driving manipulation member and the magnitude of force of driving the driving force transmission member may become a first ratio, and when the driving manipulation member is disposed at the second sliding section, the ratio may become a second ratio different from the first ratio.

PREFERRED EMBODIMENTS

First Embodiment

Figure 1:
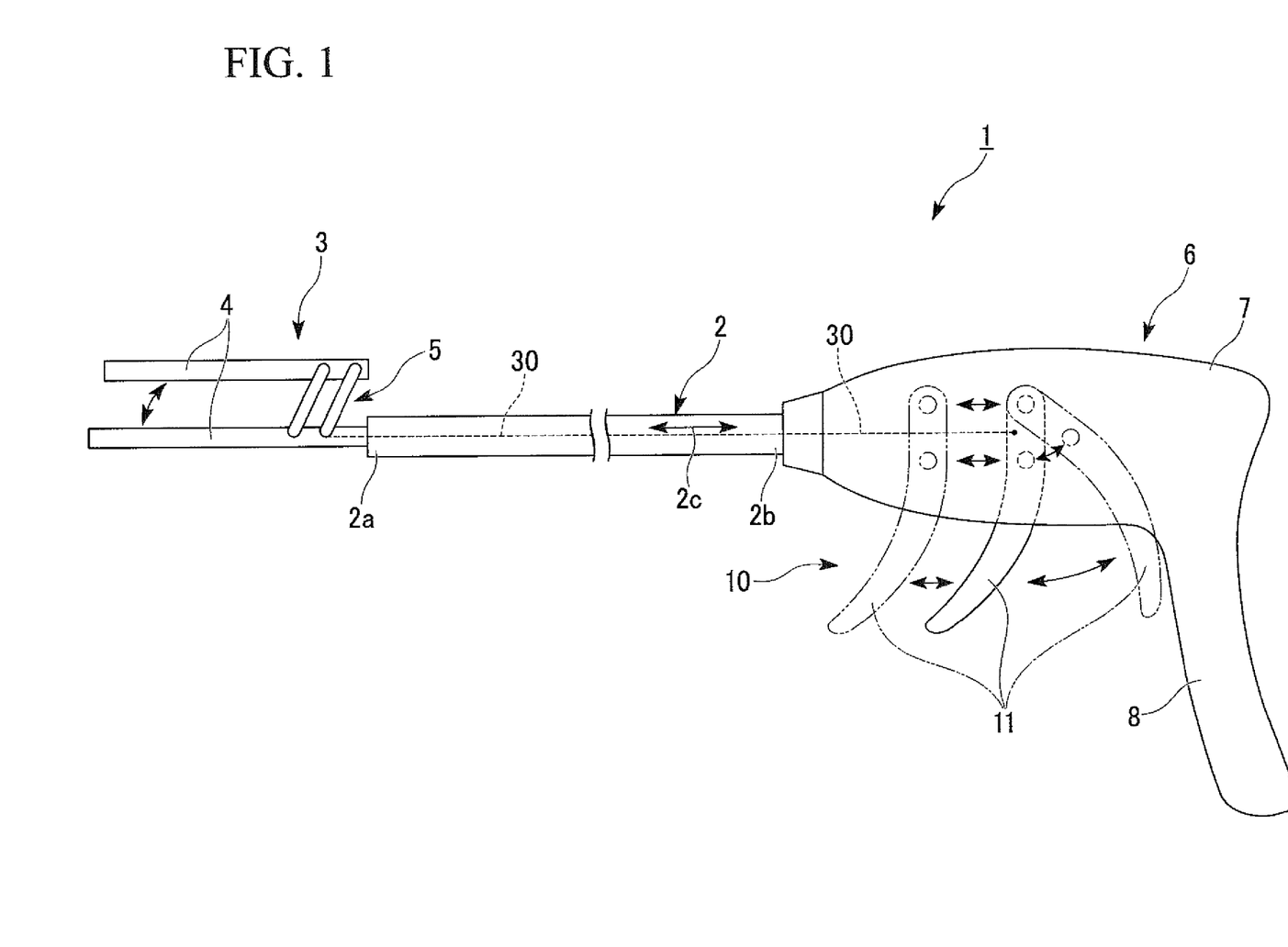
FIG. 1 is a side view showing a treatment tool according to a first embodiment of the present invention.
Figure 2:
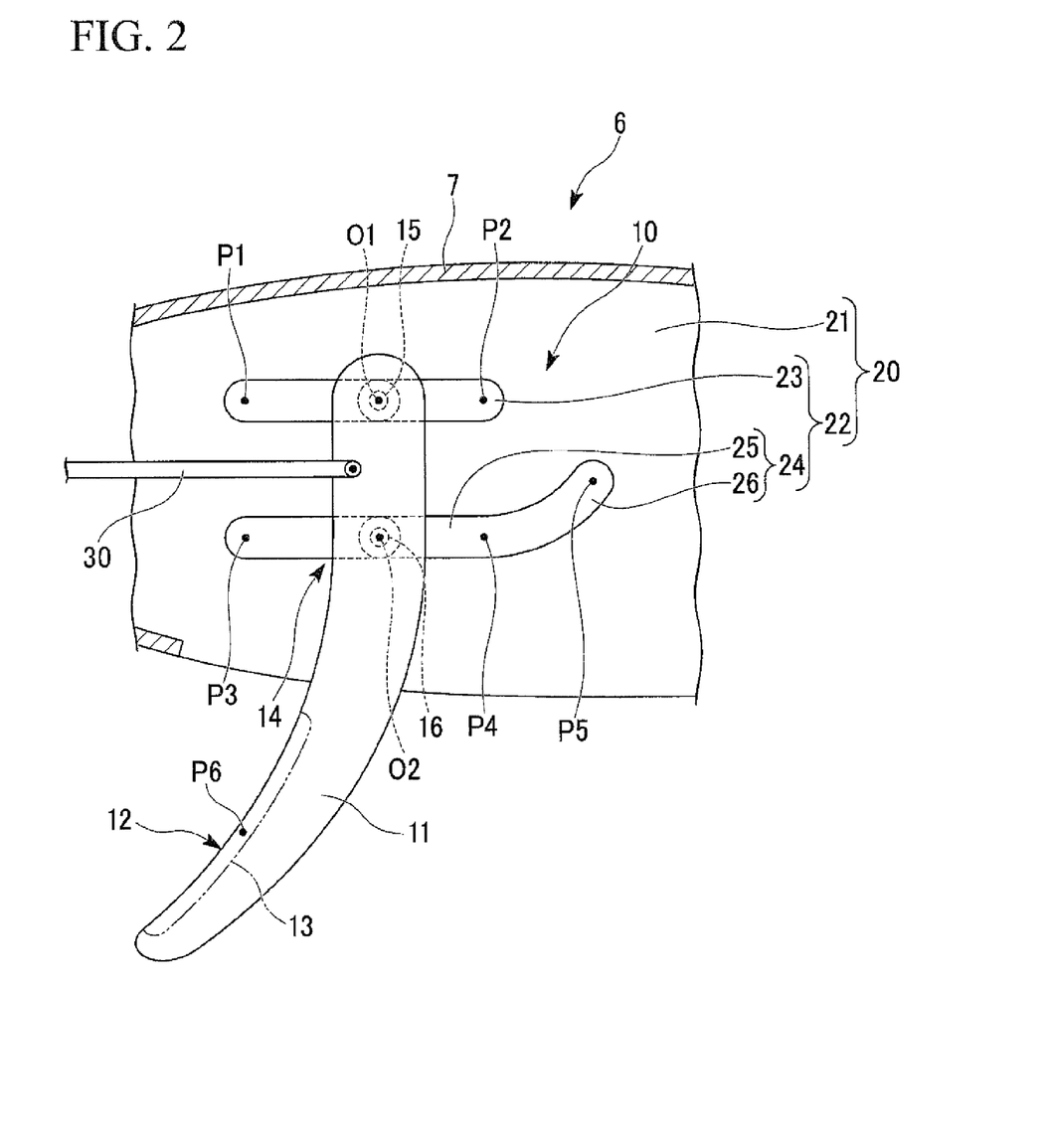
FIG. 2 is a side view showing a handle mechanism installed at the treatment tool according to the first embodiment of the present invention.
Figure 3:
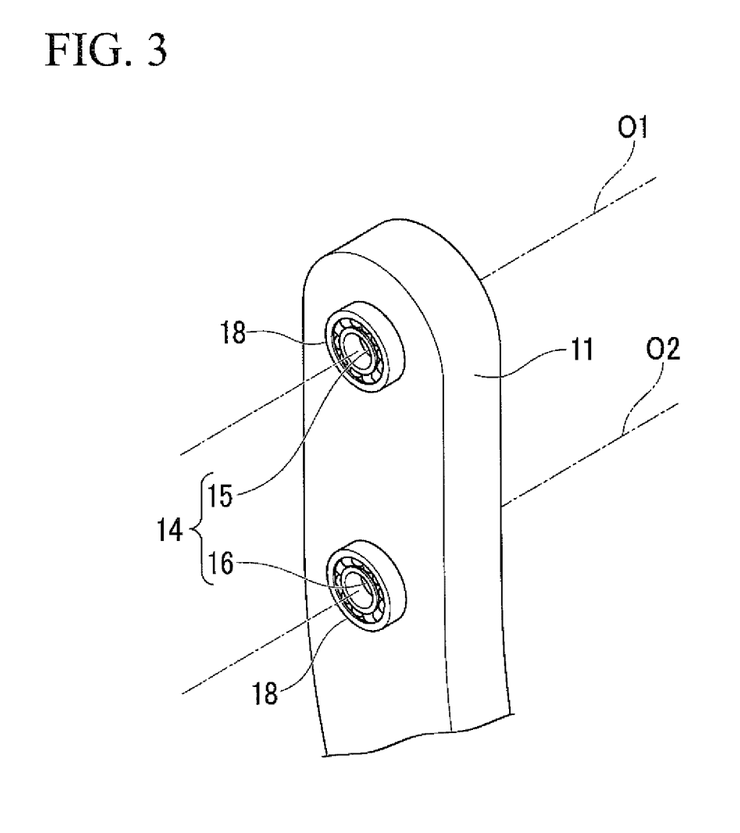
FIG. 3 is a perspective view showing a portion of a driving manipulation member installed at the handle mechanism.
Figure 4:
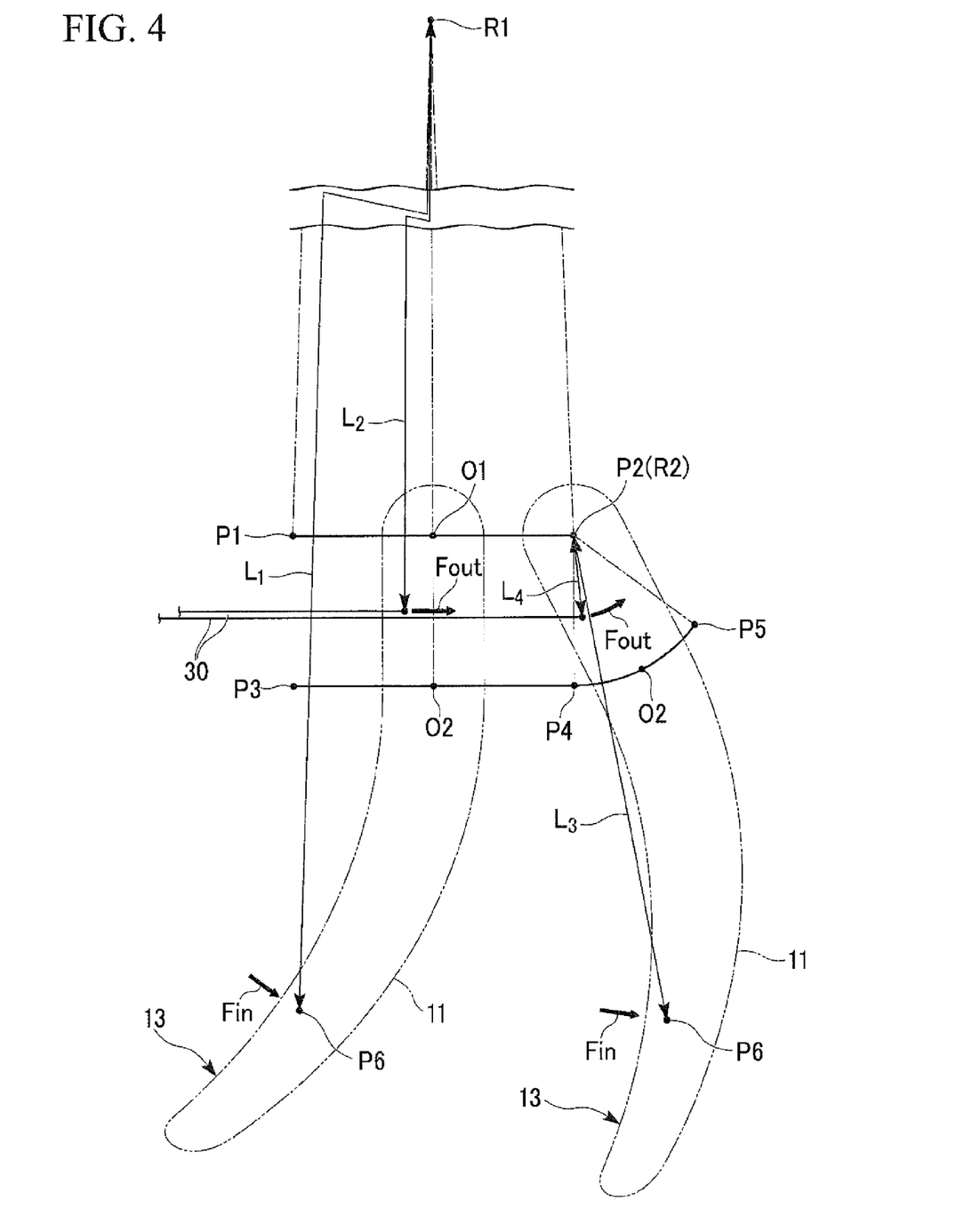
FIG. 4 is a schematic view showing an operational principal of the handle mechanism.

A treatment tool 1 of a first embodiment according to the present invention will be described. FIG. 1 is a side view of the treatment tool according to the first embodiment of the present invention. FIG. 2 is a side view showing a handle mechanism installed at the treatment tool. FIG. 3 is a perspective view showing a portion of a driving manipulation member installed at the handle mechanism. FIG. 4 is a schematic view showing an operational principle of the handle mechanism.

The treatment tool 1 includes a long insertion section (a long shaft member) 2, a treatment unit 3, a manipulation unit 6, and a driving force transmission member 30. The treatment unit 3 is installed at a distal end (a distal end portion) 2a of the insertion section 2. The manipulation unit 6 is installed at a proximal end (a proximal end portion) 2b of the insertion section 2 to manipulate the treatment unit 3. The driving force transmission member 30 is connected to the manipulation unit 6 and the treatment unit 3.

The insertion section 2 is a tubular member having flexibility, into which the driving force transmission member 30 is inserted so as to advance and retract along a longitudinal axis 2c of the insertion section 2. In the embodiment, the insertion section 2 is constituted by a coil sheath on which a flexible wire rod is wound. The insertion section 2 constituted by the coil sheath has a high tolerance with respect to compression of the insertion section 2 in a central axis direction. In addition, the insertion section 2 can transmit a rotational force when a proximal end of the insertion section 2 is rotated about a central axis as a rotational force for rotating a distal end of the insertion section 2 about the central axis.

The treatment unit 3 has a pair of jaws (a pair of grasping members) 4 opened and closed by linear movement of the driving force transmission member 30 in the central axis direction of the insertion section 2. The jaws 4 are connected to a distal end of the driving force transmission member 30 via a known link mechanism 5. A force transmitted via the driving force transmission member 30 is converted into a force for opening/closing the jaws 4 by the link mechanism 5. In the embodiment, when the driving force transmission member 30 is moved toward the distal end of the insertion section 2, the pair of jaws 4 are open (a first position), and when the driving force transmission member 30 is moved toward a proximal end of the insertion section 2, the pair of jaws 4 are closed (a second position).

In addition, the treatment unit 3 may include, instead of the pair of jaws 4 that can be opened and closed, such as other forceps, a stapler, a clip, a needle holder, and the like. In this case, the link mechanism 5 is configured to convert a linear movement of the driving force transmission member 30 into an operation of the treatment unit 3.

The manipulation unit 6 includes an exterior body (a manipulation unit main body) 7 connected to the proximal end of the insertion section 2, and a handle mechanism 10 partially installed in the exterior body 7.

A grip 8 held by an operator to manipulate a driving manipulation member 11 is formed at the exterior body 7. The grip 8 is a rod-shaped member extending in substantially the same direction as a direction in which the driving manipulation member 11 protrudes from the exterior body 7.

As shown in FIG. 2, the handle mechanism 10 includes the driving manipulation member 11, and a switch unit 20. The driving manipulation member 11 is configured to be connected to the proximal end of the driving force transmission member 30 in the exterior body 7 and protrude to the outside of the exterior body 7. The switch unit 20 is installed in the exterior body 7 and connected to the driving manipulation member 11 in the exterior body 7.

The driving manipulation member 11 includes a trigger section 12 on which an operator's finger is set, and a connecting section 14 connected to the switch unit 20.

A portion of the trigger section 12 within a range with which the operator's finger can come in contact when the operator manipulates the treatment tool 1 using the trigger section 12, constitutes an input section 13 into which a manipulation amount is input by the operator. A leverage point P6 based on design is previously determined on the input section 13. The switch unit 20 is designed on the assumption that the operator applies a force to the leverage point P6 based on design.

The driving manipulation member 11 is moved with respect to the exterior body 7 of the manipulation unit 6 by the operator's finger put on the trigger section 12.

As shown in FIGS. 2 and 3, the connecting section 14 has a first pin 15 and a second pin 16 disposed in the exterior body 7. The first pin 15 and the second pin 16 are substantially columnar shaped members having central axes O1 and O2 parallel to each other. In the embodiment, bearings 18 rotatable about the central axes O1 and O2 as rotational centers are inserted into the first pin 15 and the second pin 16. In the embodiment, the bearings 18 have outer circumferential surfaces formed columnar and are rotated about the rotational center upon contact with slide rails 22 (to be described later).

As shown in FIG. 2, the switch unit 20 is installed at the manipulation unit 6 in an attempt to get the treatment unit 3 to be operated between the first position and the second position and to switch a ratio of a movement amount of the driving force transmission member 30 with respect to a movement amount of the driving manipulation member 11. The switch unit 20 has a base 21 disposed in the manipulation unit 6 and fixed to the manipulation unit 6, and the slide rails (a first sliding section, a second sliding section) 22 installed at the base 21.

The slide rails 22 formed at the base 21 include a first slide rail 23 and a second slide rail 24. The first slide rail 23 is a linear slide rail extending to be parallel to a direction in which the insertion section 2 protrudes from the manipulation unit 6. The second slide rail 24 is a slide rail formed at a position spaced apart from the first slide rail 23.

The first slide rail 23 is a groove or a through-hole formed in the base 21. In the first slide rail 23, a pair of inner surfaces extending in a longitudinal direction of the first slide rail 23 is parallel to each other. A distance between the pair of inner surfaces is slightly larger than an outer dimension of the bearing 18 attached to the first pin 15.

As an outer circumferential surface of the bearing 18 attached to the first pin 15 comes in contact with an inner surface of the first slide rail 23, the first pin 15 is guided in the longitudinal direction of the first slide rail 23.

The second slide rail 24 is configured by a groove or a through-hole formed in the base 21. The second slide rail 24 has a linear section 25 parallel to the first slide rail 23, and an arc-shaped section 26 connected to the linear section 25.

The second pin 16 to which the bearing 18 is attached is inserted into the linear section 25 and the arc-shaped section 26, and an outer circumferential surface of the bearing 18 attached to the second pin 16 comes in contact with an inner surface of the linear section 25 or the arc-shaped section 26.

The arc-shaped section 26 is formed in an arc shape centered on an end section of the proximal end side of the first slide rail 23. Specifically, a position of a central axis of the first pin 15 when the bearing 18 of the first pin 15 abuts the end section of the proximal end side of the first slide rail 23 is positioned at a center of an arc portion of the arc-shaped section 26. An end section of the arc-shaped section 26 opposite to a side thereof connected to the linear section 25 has a semi-circular shape conforming to a shape of the outer circumferential surface of the bearing 18.

A distance between the first slide rail 23 and the second slide rail 24 is substantially equal to a distance between the first pin 15 and the second pin 16. The driving manipulation member 11 into which the second pin 16 and the first pin 15 are inserted is supported in the linear section 25 of the second slide rail 24 and the first slide rail 23 such that the driving manipulation member 11 can be linearly moved. Moreover, the driving manipulation member 11 is supported in the arc-shaped section 26 of the second slide rail 24 and the first slide rail 23. The driving manipulation member 11 is supported by the slide rail such that the second pin 16 can be pivoted along the arc-shaped section 26 about the central axis of the first pin 15.

When the first pin 15 is positioned at the end section of the distal end side of the first slide rail 23 and the second pin 16 is positioned at the end section of the distal end side of the second slide rail 24, the pair of jaws 4 are completely open. In the embodiment, this position is referred to as "a start position."

In addition, as the driving manipulation member 11 is moved along the slide rails 22, when the first pin 15 is positioned at the end section of the proximal end side of the first slide rail 23 and the second pin 16 is positioned at the end section of the proximal end side of the second slide rail 24, the pair of jaws 4 are completely closed. In the embodiment, this position is referred to as "an end position."

In the embodiment, the driving manipulation member 11 is moved with respect to the manipulation unit 6 in substantially one direction between the start position and the end position.

In addition, in the embodiment, the second slide rail 24 of the slide rails 22 has a shape in which the linear section 25 and the arc-shaped section 26 are formed continuously each other. For this reason, a moving direction in which the driving manipulation member 11 is moved along the linear section 25 and a direction in which the driving manipulation member 11 is moved along the arc-shaped section 26 are not one direction in the strict sense. In the embodiment, "the approximately one direction" includes the case in which the moving direction is varied such that the moving direction of the driving manipulation member 11 is not reversed when the driving manipulation member 11 is moved from the start position to the end position or when the driving manipulation member 11 is moved from the end position to the start position.

A rotational center switch unit configured to switch a rotational center of the driving manipulation member 11 is constituted by the first pin 15 and the second pin 16 which are formed at the driving manipulation member 11, and the first slide rail 23 and the second slide rail 24 which are formed at the base 21.

In the embodiment, the first slide rail 23 is formed linearly, and the linear section 25 of the second slide rail 24 is formed linearly in parallel with the first slide rail 23. As shown in FIGS. 2 and 4, the driving manipulation member 11 in a state in which the first pin 15 is inserted into the first slide rail 23 and the second pin 16 is inserted into the linear section 25 may be said to be rotated about an imaginary rotational center disposed at a position spaced an infinite distance from the first slide rail 23.

In the embodiment, the imaginary rotational center is referred to as a first rotational center R1, and a position of the central axis of the first pin 15 when the first pin 15 is disposed at the end section of the proximal end side of the first slide rail 23 is referred to as a second rotational center R2. In addition, in the embodiment, a state in which the driving manipulation member 11 is rotated about the first rotational center R1 is referred to as a first state, and a state in which the driving manipulation member 11 is rotated about the second rotational center R2 is referred to as a second state.

The rotational center switch unit switches a rotational center of the driving manipulation member 11 with respect to the manipulation unit 6 from the first rotational center R1 to the second rotational center R2 or from the second rotational center R2 to the first rotational center R1 at a position between the start position and the end position, and at a boundary between the linear section 25 and the arc-shaped section 26. That is, the first state and the second state are switched by the rotational center switch unit.

As shown in FIGS. 1 and 2, the driving force transmission member 30 is formed of a wire rod having flexibility and high strength against compression or tension in the central axis direction. The driving force transmission member 30 is pulled by the driving manipulation member 11, and transmits a force needed to drive the treatment unit 3 from the manipulation unit 6 to the treatment unit 3.

Next, in a configuration of a major part of the handle mechanism 10, a magnitude correlation of the force when the rotational center is switched by the rotational center switch unit will be described with reference to FIG. 4.

The handle mechanism 10 according to the embodiment is designed on the assumption that a force is applied from the operator to the leverage point P6 based on design of the input section 13. A magnitude of a force applied to the driving manipulation member 11 by the operator is set as $F_{in}$. A magnitude of a force driven by the driving force transmission member 30 via the switch unit 20 is set as $F_{out}$. A distance between the leverage point P6 of the input section 13 and the first rotational center R1 is set as $L_1$. A distance between a connecting position at which the driving force transmission member 30 is connected to the driving manipulation member 11 and the first rotational center R1 is set as $L_2$. A distance between the leverage point P6 of the input section 13 and the second rotational center R2 is set as $L_3$. A distance between the connecting position and the second rotational center R2 is set as $L_4$. Here, a relational expression in the first state is $F_{out}/F_{in}=L_1/L_2$, and a relational expression in the second state is $F_{out}/F_{in}=L_3/L_4$.

In addition, in the embodiment, the relational expression of them is $L_1/L_2<L_3/L_4$. That is, in the second state, in comparison with the first state, a force applied to the driving force transmission member 30 is larger than a force input to the input section 13. This is because the input to the input section 13 is reduced to be transmitted to the driving force transmission member 30 according to the principle of leverage.

An operation of the handle mechanism 10 having the above-mentioned configuration will be described along with an operation of the treatment tool 1 in use.

When using the treatment tool 1, for example, the treatment tool 1 is set in a treatment tool channel of a flexible endoscope (not shown), and guides the treatment unit 3 to a treatment target.

The operator of the treatment tool 1 grips the grip 8 of the manipulation unit 6, puts his/her finger on the driving manipulation member 11 protruding from the exterior body 7, and moves the driving manipulation member 11 with respect to the manipulation unit 6 in a desired direction. For example, when the driving manipulation member 11 is moved from the start position to the end position, the driving force transmission member 30 is moved in a direction from the distal end of the insertion section 2 toward the proximal end by the force moving the driving manipulation member 11, and the pair of jaws 4 are changed from a completely open state (a first position) to a completely closed state (a second position). When the pair of jaws 4 are in the completely closed state, the second pin 16 is disposed slightly closer to the distal end side than the end section of the proximal end side of the arc-shaped section 26. For this reason, when the driving manipulation member 11 is further moved until the bearing 18 of the second pin 16 comes in contact with the end section of the proximal end side of the arc-shaped section 26, a force in a closing direction of the pair of jaws 4 can be applied to the pair of jaws 4 in the completely closed state. Accordingly, the pair of jaws 4 can be securely closed even when expansion and contraction of the insertion section 2 or expansion and contraction of the driving force transmission member 30 occur.

For example, while the driving manipulation member 11 is moved with respect to the manipulation unit 6 from the start position to the end position, the moving state of the driving manipulation member 11 with respect to the manipulation unit 6 is switched from the first state to the second state by the switch unit 20. Specifically, the moving state of the driving manipulation member 11 with respect to the manipulation unit 6 is switched from the first state in which the driving manipulation member 11 is rotated with respect to the manipulation unit 6 about the first rotational center R1 to the second state in which the driving manipulation member 11 is rotated with respect to the manipulation unit 6 about the second rotational center R2 different from the first rotational center R1. In the first state, a movement amount of the driving manipulation member 11 is equal to a movement amount of the driving force transmission member 30. In addition, in the second state, the movement amount of the driving force transmission member 30 is smaller than that of the driving manipulation member 11. In the second state, the movement amount of the driving force transmission member 30 is reduced with respect to the movement amount of the driving manipulation member 11 and a force applied to the treatment unit 3 is increased accordingly. For this reason, in the second state, the gripping target can be gripped by the pair of jaws 4 with a force larger than that of the first state. In addition, in the first state, the pair of jaws 4 can be rapidly moved in a state in which the gripping target is not separately gripped.

Since the conventional handle mechanism has not have a mechanism for varying a reduction ratio between the first state and the second state, even when a range in which a large force needs to be applied and a range in which rapid movement is preferable are provided, the moving speed of the treatment unit with respect to the moving speed of the driving manipulation member or the force applied to the driving manipulation member by the operator and the force of operating the treatment unit are not varied from a constant relation.

On the other hand, according to the handle mechanism 10 of the embodiment, a mechanism for varying a reduction ratio between the first state and the second state is provided. For this reason, each of the jaws 4 can be rapidly moved in the first state at a position near the position where a position in the state that the pair of jaws 4 are completely opened within the movable range in which the pair of jaws 4 are opened and closed, and a larger force than that of the first state can be applied to the pair of jaws 4 in the second state at a position near the position where a position in a state that the pair of jaws 4 are completely closed within the movable range in which the pair of jaws 4 are opened and closed. During the treatment, for example, the gripping target having elasticity such as a biological tissue or the like may be grasped using the pair of jaws 4 by closing the pair of jaws 4. Here, as the jaws approach the completely closed state, the force required to close the pair of jaws 4 is increased. For this reason, as described in the embodiment, the gripping target can be appropriately grasped by only moving the driving manipulation member 11 substantially in one direction within a state that the pair of jaws 4 are positioned from the completely open state to the completely closed state.

In addition, in the first state, a circumstance in which the driving manipulation member 11 cannot be easily moved due to elasticity of the gripping target harder occurs than the ease in which the gripping target is grasped by the pair of jaws 4 in the second state. Accordingly, even when the movement amount of the driving manipulation member 11 is set to be smaller than that of the driving force transmission member 30, probability that a force for opening or closing the pair of jaws 4 become insufficient is low.

In the embodiment, the movable range of the driving manipulation member 11 with respect to the manipulation unit 6 is preferably within a range in which the driving manipulation member 11 can be moved by the operator opens or closes his/her hand. For this reason, the movable range of the driving manipulation member 11 has an upper limit. Here, as the movement amount of moving the driving manipulation member 11 is reduced in the first state, the movement amount of moving the driving manipulation member 11 can be set to be large in the second state. For this reason, even in a state in which the movable range of the driving manipulation member 11 is limited, the opening/closing movement amount of the pair of jaws 4 can be sufficiently secured and a force having a sufficient magnitude with respect to the pair of jaws 4 can be applied.

In addition, in the first state, the driving manipulation member 11 is actually moved linearly because the first rotational center R1 is disposed at a position of an infinite distance. For this reason, the driving manipulation member 11 is moved linearly in the first state and rotated in the second state, and movement of the driving manipulation member 11 is remarkably changed at a position at which the first state and the second state are switched. As a result, the operator who manipulates the treatment tool 1 can easily recognize whether the handle mechanism 10 is in the first state or the second state.

First Modified Example

Figure 5:
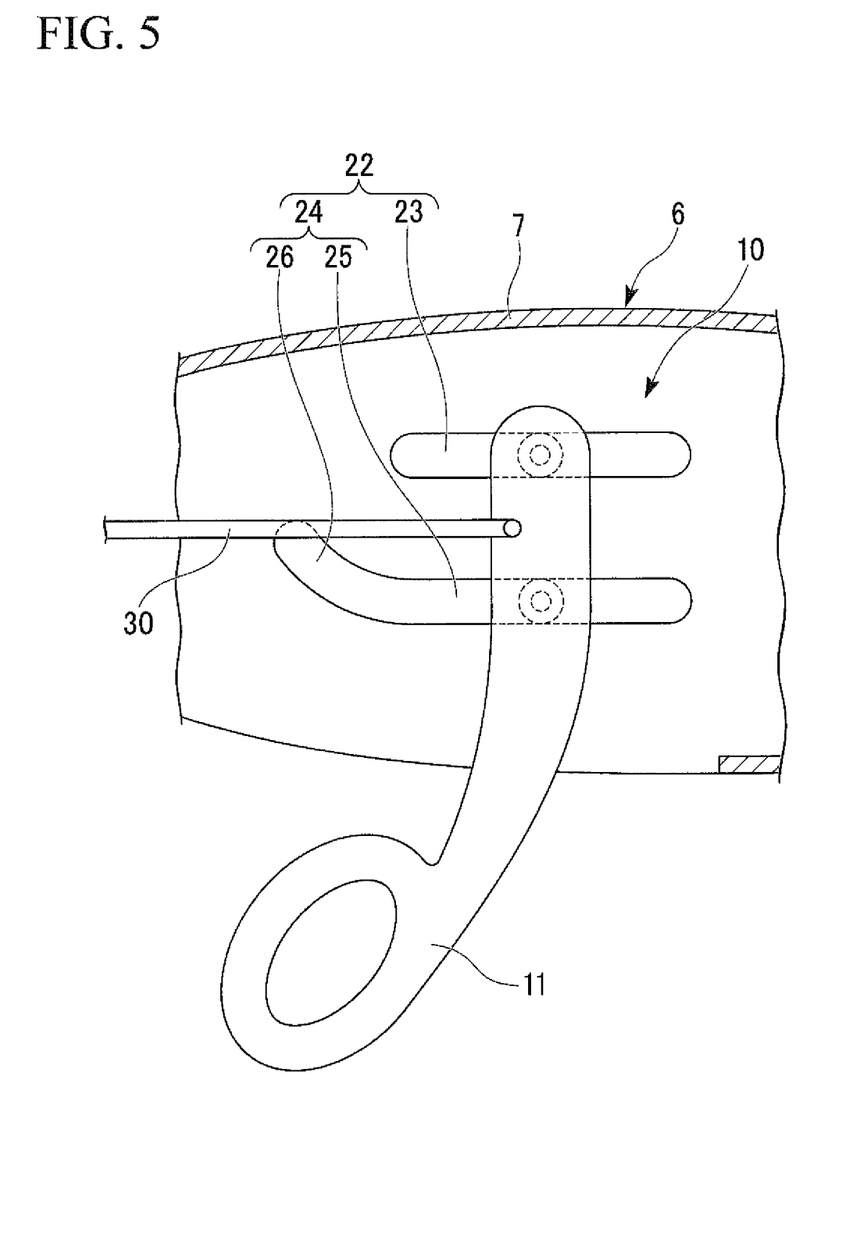
FIG. 5 is a side view showing a handle mechanism according to a first modified example of the present invention.

Next, a first modified example of the handle mechanism 10 described in the above-mentioned first embodiment will be described with reference to FIG. 5. FIG. 5 is a side view showing a handle mechanism of the modified example.

As shown in FIG. 5, the modified example is different from the above-mentioned first embodiment in that the handle mechanism 10 is reversely disposed back and forth. That is, the arc-shaped section 26 of the second slide rail 24 is disposed at the distal end side of the manipulation unit 6.

In addition, in the case of the modified example, the driving manipulation member 11 has a shape so as to easily hook a finger while the driving manipulation member 11 is pushed toward the distal end. Specifically, a ring portion through which a finger can pass is formed at the driving manipulation member 11.

Even in the above-mentioned configuration, the same effect as the handle mechanism 10 described in the first embodiment is exhibited.

Further, in the case of the modified example, if the driving manipulation member 11 is moved from the distal end side to the proximal end side of the manipulation unit 6, when the position of the second pin 16 is switched from the arc-shaped section 26 to the linear section 25 of the second slide rail 24, a magnitude of force required for the operator to manipulate the driving manipulation member 11 is increased. Accordingly, the operator can recognize that the operator has been operated a given amount of work for which the driving manipulation member 11 is moved to reach the proximal end through a feeling of the finger in contact with the driving manipulation member 11.

For example, in the grasping forceps or the like, as a magnitude of force for manipulation is switched as described above, the operator can recognize that the operator has gripped the driving manipulation member 11 with a given amount of distance. That is, the operator can recognize that the grasping forceps is closed until a predetermined position. Accordingly, it is possible to suppress to grasp the biological tissue or the like with an excessively strong force by the grasping forceps.

Second Modified Example

Figure 6:
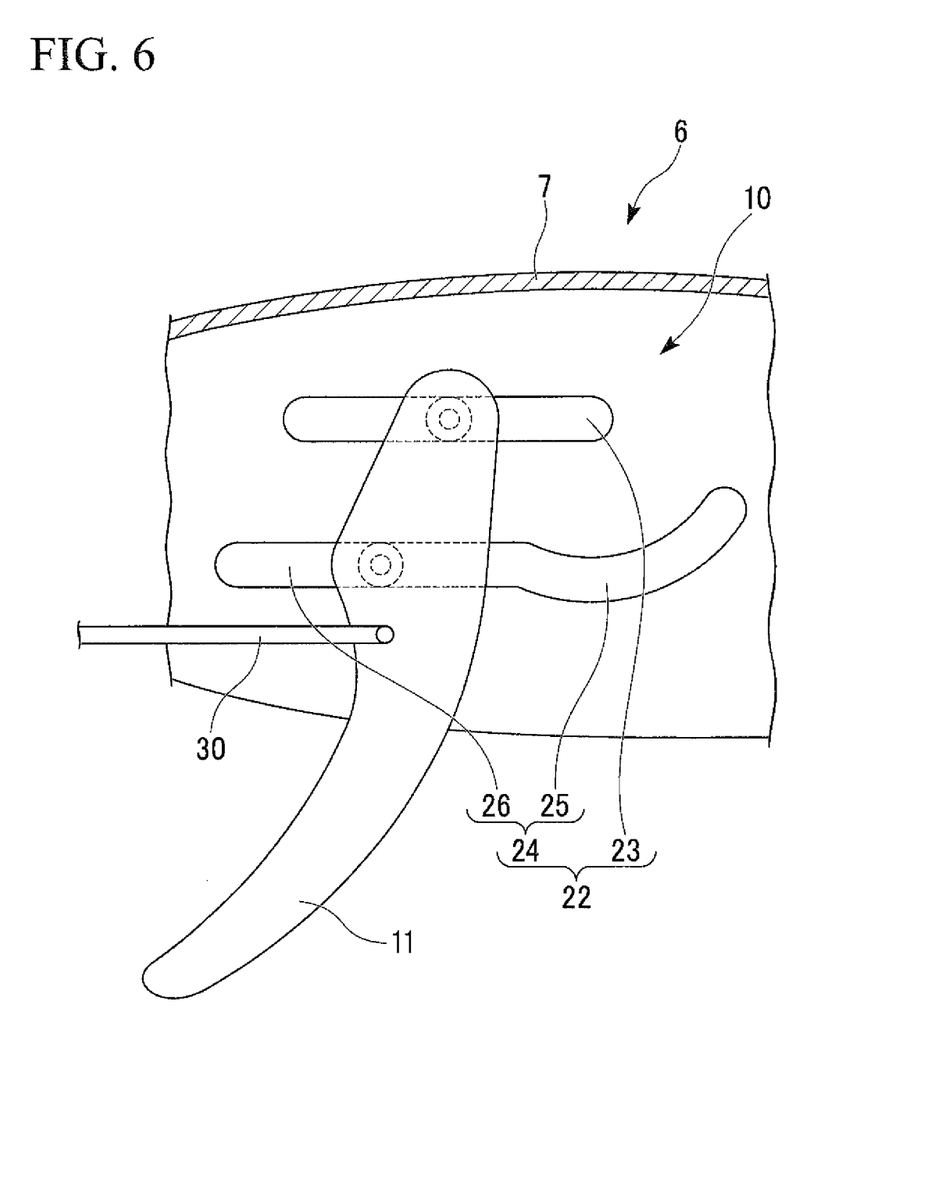
FIG. 6 is a side view showing a handle mechanism according to a second modified example of the present invention.

Next, a second modified example of the handle mechanism 10 described in the above-mentioned first embodiment will be described with reference to FIG. 6. FIG. 6 is a side view showing a handle mechanism of the modified example.

As shown in FIG. 6, the modified example is different from the above-mentioned first embodiment in that a radius of the arc-shaped section 26 is larger than that of the arc-shaped section 26 of the first embodiment. In addition, the linear section 25 of the second slide rail 24 is offset closer to the distal end side than the linear section 25 described in the first embodiment.

Even in the above-mentioned configuration, the same effect as the handle mechanism 10 described in the first embodiment is exhibited.

Third Modified Example

Figure 7:
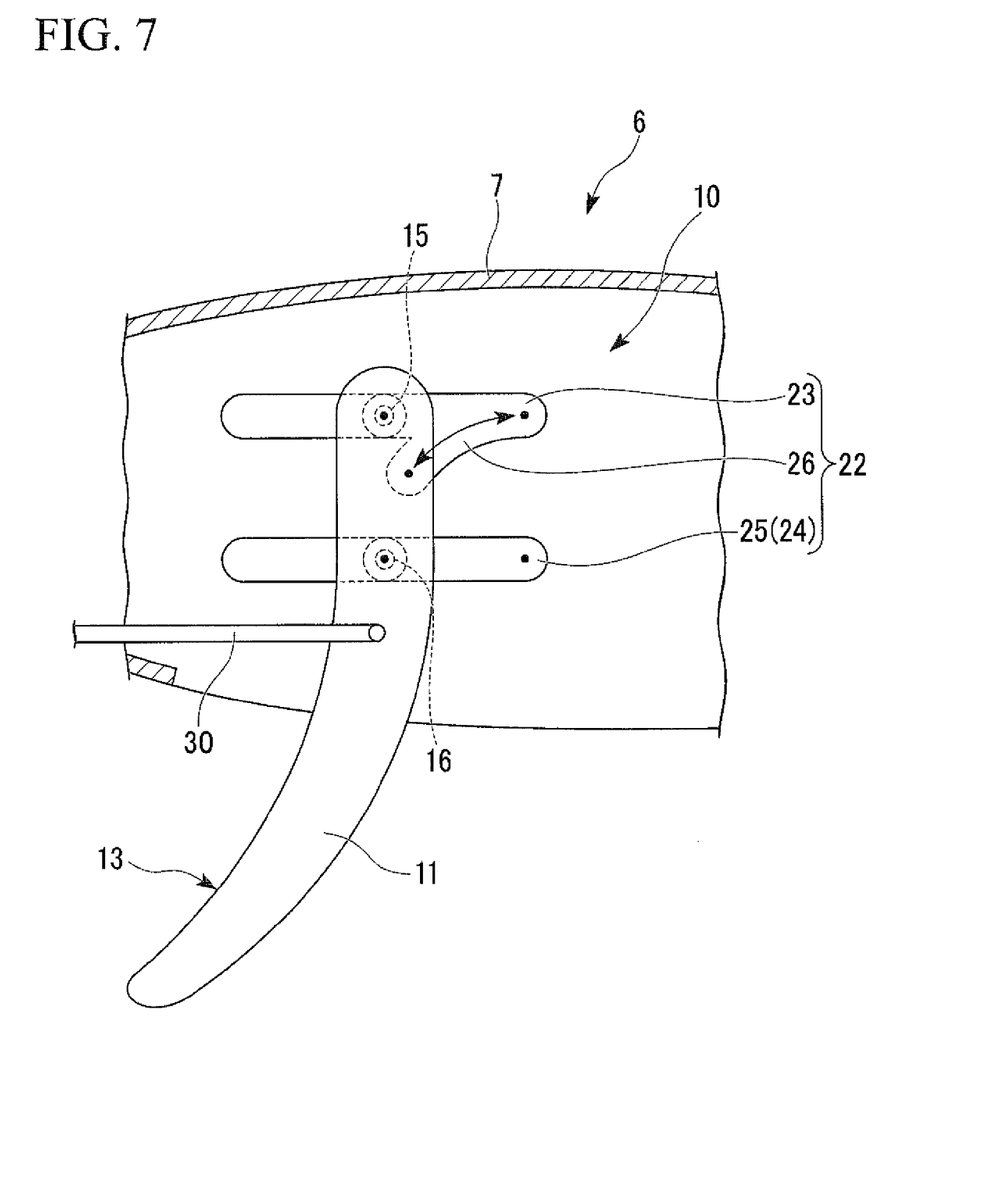
FIG. 7 is a side view showing a handle mechanism according to a third modified example of the present invention.

Next, a third modified example of the handle mechanism 10 described in the above-mentioned first embodiment will be described with reference to FIG. 7. FIG. 7 is a side view showing a handle mechanism of the modified example.

As shown in FIG. 7, the modified example is different from the first embodiment in that the arc-shaped section 26 is formed at the first slide rail 23. That is, in the case of the modified example, the second pin 16 is supported at the end section of the proximal end side of the linear section 25 of the second slide rail 24. Then, a position of the central axis of the second pin 16 is a rotary shaft corresponding to the second rotational center R2 described in the above-mentioned first embodiment. In a state in which the second pin 16 is supported at the end section of the proximal end side of the linear section 25 of the second slide rail 24, when the input section 13 of the driving manipulation member 11 is moved toward the proximal end side of the manipulation unit 6, the first pin 15 is moved toward the distal end along the arc-shaped section 26 about a position of the central axis of the second pin 16 as a rotational center.

Even in the above-mentioned configuration, the same effect as the handle mechanism 10 described in the first embodiment is exhibited.

In addition, since the arc-shaped section 26 is disposed between the first slide rail 23 and the linear section 25, the handle mechanism 10 can be miniaturized compared to the first embodiment.

Second Embodiment

Figure 8:
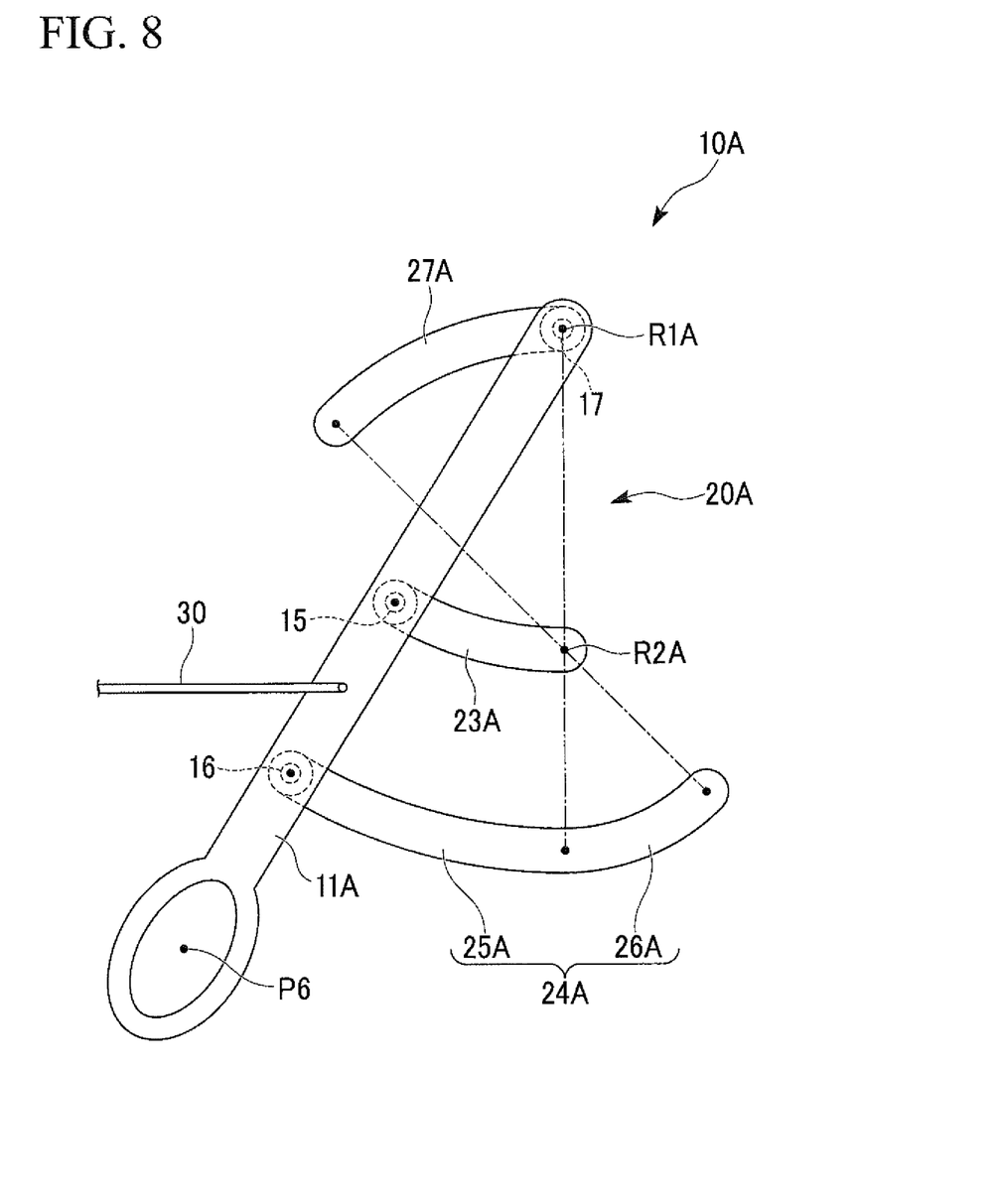
FIG. 8 is a side view showing a handle mechanism according to a second embodiment of the present invention.

Next, a handle mechanism 10A of a second embodiment of the present invention will be described. Hereinafter, the same components as those described in the above-mentioned first embodiment are designated by the same reference numerals, and description thereof will be omitted. FIG. 8 is a side view showing a handle mechanism according to the embodiment.

As shown in FIG. 8, unlike the first embodiment, the handle mechanism 10A includes a driving manipulation member 11A instead of the driving manipulation member 11, and a switch unit 20A instead of the switch unit 20.

The driving manipulation member 11A further includes a third pin 17 in addition to the first pin 15 and the second pin 16. The first pin 15, the second pin 16 and the third pin 17 are disposed in parallel on a straight line. The above-mentioned bearing 18 (see FIG. 3) is attached to the third pin 17.

The switch unit 20A includes a first slide rail 23A, a second slide rail 24A and a third slide rail 27A. The first slide rail 23A is formed in an arc shape about a first rotational center R1A set at a position different from the first rotational center R1. The second slide rail 24A and the third slide rail 27A are formed apart from the first slide rail 23A.

The second slide rail 24A includes a first arc-shaped section 25A and a second arc-shaped section 26A. The first arc-shaped section 25A is concentrically formed with the first slide rail 23A, and formed in an arc shape parallel to the first slide rail 23A. The second arc-shaped section 26A is formed in an arc shape having a larger radius of curvature than that of the first arc-shaped section 25A.

The third slide rail 27A is formed in an arc shape concentric with the second arc-shaped section 26A. The end section of the proximal end side of the third slide rail 27A is disposed on a straight line passing through a boundary between the first arc-shaped section 25A and the second arc-shaped section 26A, and the end section of the proximal end side of the first slide rail 23A. The end section of the distal end side of the third slide rail 27A is disposed on a straight line passing through the end section of the proximal end side of the second arc-shaped section 26A and the end section of the proximal end side of the first slide rail 23A.

In the embodiment, a state in which the second pin 16 is moved along the first arc-shaped section 25A is a first state in which the driving manipulation member 11A is moved about the first rotational center R1A. In addition, a state in which the second pin 16 is moved along the second arc-shaped section 26A is a second state in which the driving manipulation member 11A is moved about the second rotational center R2A.

In the embodiment, similar to the first embodiment, a relational expression in the first state is $F_{out}/F_{in}=L_1/L_2$, and a relational expression in the second state is $F_{out}/F_{in}=L_3/L_4$. In the embodiment, a relational expression is $L_1/L_2<L_3/L_4$.

Next, an operation of the handle mechanism 10 according to the embodiment will be described.

A center of the arc of the third slide rail 27A is the above-mentioned second rotational center R2A, and the third pin 17 is fixed to the end section of the proximal end side of the third slide rail 27A until the first pin 15 is moved to the end section of the proximal end side of the first slide rail 23A.

When the driving manipulation member 11A is moved until the first pin 15 comes in contact with the end section of the proximal end side of the first slide rail 23A, the second pin 16 is positioned at a boundary between the first arc-shaped section 25A and the second arc-shaped section 26A. After that, when the driving manipulation member 11A is further moved, the second pin 16 is moved toward the proximal end of the second arc-shaped section 26A. Here, since the third slide rail 27A is formed in an arc shape having the same rotational center as the second arc-shaped section 26A, the driving manipulation member 11A is rotated about a position of the central axis of the first pin 15 in contact with the end section of the proximal end side of the first slide rail 23A as a rotational center.

Even in the embodiment, similar to the handle mechanism 10 of the first embodiment, a reduction ratio between the first state and the second state is varied.

In addition, the first pin 15, the second pin 16 and the third pin 17 may not be disposed in parallel on the same straight line.

Fourth Modified Example

Figure 9:
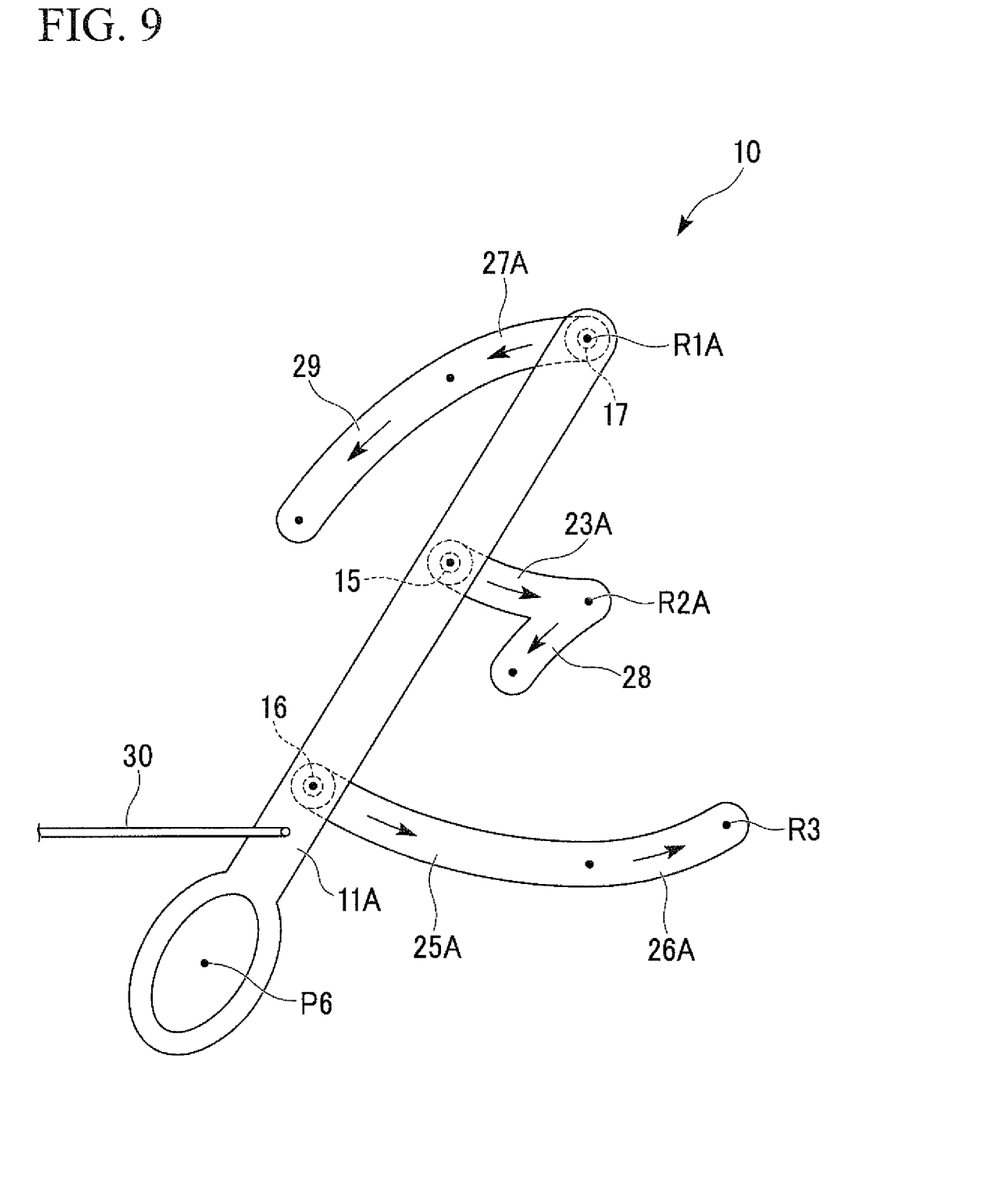
FIG. 9 is a side view showing a handle mechanism according to a fourth modified example of the present invention.

Next, a modified example of the handle mechanism 10A described in the second embodiment will be described with reference to FIG. 9. FIG. 9 is a side view showing a handle mechanism of the modified example.

As shown in FIG. 9, in the modified example, a fourth slide rail 28 branched off from the proximal end of the first slide rail 23A, formed in an arc shape about the proximal end of the second arc-shaped section 26A and extending toward the distal end side is provided with the first slide rail 23A. Further, a third arc-shaped section 29 positioned closer to the distal end side than the distal end of the third slide rail 27A described in the second embodiment and formed in an arc shape having the same rotational center as the fourth slide rail 28 is formed at the third slide rail 27A.

In the modified example, when the driving manipulation member 11A is further moved toward the proximal end from a state in which the second pin 16 is positioned at the end section of the proximal end side of the second arc-shaped section 26A, the driving manipulation member 11A is rotated about a position of the central axis of the second pin 16 as a rotational center. A position of the central axis of the second pin 16 in a state in which the second pin 16 is positioned at the end section of the proximal end side of the second arc-shaped section 26A is a third rotational center R3 configured to transmit a force to the driving force transmission member 30 from the driving manipulation member 11A at a reduction ratio different from the first state and second state. Hereinafter, a state in which the driving manipulation member 11 is rotated about the third rotational center R3 is referred to as "a third state."

In the case of the modified example, when the driving manipulation member 11A is moved from the distal end side toward the proximal end substantially in one direction, the first state in which the driving manipulation member 11 is rotated about the first rotational center R1A, the second state in which the driving manipulation member 11 is rotated about the second rotational center R2A, and the third state in which the driving manipulation member 11 is rotated about the third rotational center R3 are sequentially switched. Accordingly, the magnitude of the force applied to the treatment unit 3 including the pair of jaws 4 or the like can be switched in three stages.

In addition, as the slide rails having different radii of curvature are combined, the switching of the magnitude of the force applied to the treatment unit 3 may be performed in more than three stages.

Third Embodiment

Figure 10:
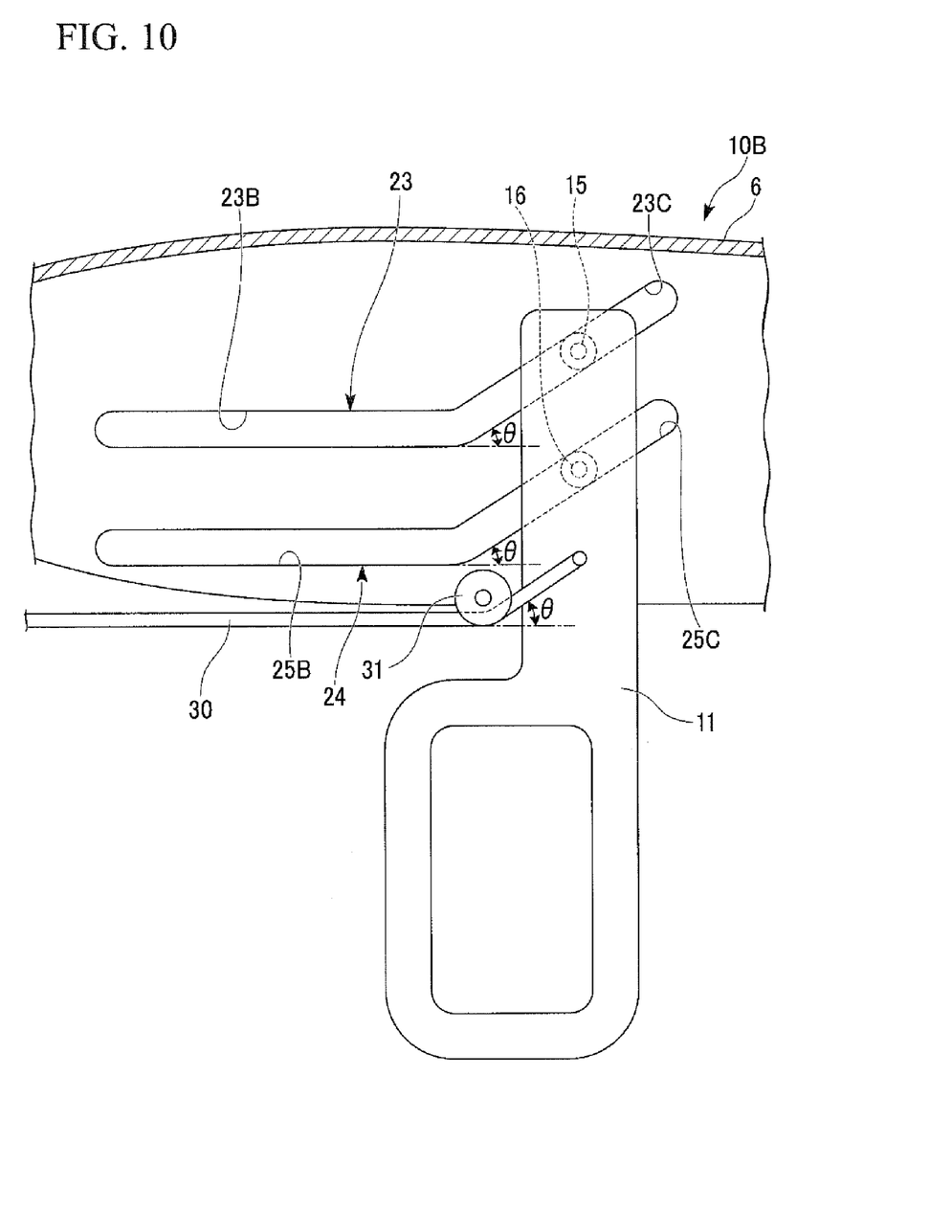
FIG. 10 is a side view showing a handle mechanism according to a third embodiment of the present invention.

Next, a treatment tool according to a third embodiment of the present invention will be described. FIG. 10 is a side view showing a handle mechanism 10B according to the embodiment.

As shown in FIG. 10, the handle mechanism 10B according to the embodiment is different from the first embodiment in that the driving manipulation member 11 is moved linearly in both of the first state and the second state described in the above-mentioned first embodiment.

That is, in the handle mechanism 10B, the first slide rail 23 has a linear section 23B formed at a distal end side of the manipulation unit 6 and a second linear section 23C formed at a proximal end side of the manipulation unit 6, and the second slide rail 24 has a linear section 25B formed at the distal end side of the manipulation unit 6 and a second linear section 25C formed at the proximal end side of the manipulation unit 6.

The second linear sections 23C and 25C are inclined with respect to the linear sections 23B and 25B by an angle θ, respectively. That is, the first slide rail 23 and the second slide rail 24 are formed in parallel between the distal end side and the proximal end side of the manipulation unit 6.

In addition, a pulley 31 having an outer surface in contact with the driving force transmission member 30 is fixed to the manipulation unit 6. The pulley 31 is disposed near a boundary portion between the linear section 25B and the second linear section 25C.

Next, an operation of the handle mechanism 10B will be described.

When the driving manipulation member 11 is moved from the distal end to the proximal end of the manipulation unit 6, first, the driving manipulation member 11 is moved linearly along the linear sections 23B and 25B of the first slide rail 23 and the second slide rail 24. Then, the first pin 15 and the second pin 16 installed at the driving manipulation member 11 are moved to the second linear sections 23C and 25C from the linear sections 23B and 25B. Then, the moving direction of the driving manipulation member 11 is varied by the angle θ. In addition, when the proximal end of the driving force transmission member 30 is moved closer to the proximal end side of the manipulation unit 6 than the pulley 31, the driving force transmission member 30 comes in contact with the outer surface of the pulley 31. The driving force transmission member 30 in contact with the outer surface of the pulley 31 is in a state bent by the pulley 31 to the angle θ.

Accordingly, in the second linear sections 23C and 25C, the driving force transmission member 30 is pulled in a state in which a reduction ratio is reduced to arrive at 1:(1/cos θ) with respect to the linear sections.

In the treatment tool according to the embodiment, when the operator grips the handle mechanism 10B until quantity of movement of the handle mechanism 10B becomes a given amount, the handle mechanism 10B is switched to a low reduction ratio. Here, since a magnitude of force required for the operator to operate the handle is increased, the operator can instinctively recognize that the operator has operated the handle until quantity of movement of the handle mechanism 10B becomes a given amount.

In addition, similar to first modified example, the second linear sections may be disposed at the distal end side of the manipulation unit 6. In this case, as the driving manipulation member 11 is moved from the distal end to the proximal end, a manipulation feeling is varied to be lighter.

Hereinabove, while the exemplary embodiments of the present invention have been described, the present invention is not limited to these embodiments. Addition, omission, substitution, and other modifications of components can be made without departing from the spirit of the present invention.

For example, in addition to the configurations described in the above-mentioned embodiments and the modified examples, a configuration in which a first state is a state in which the driving manipulation member is rotated and a second state is a state in which the driving manipulation member is moved linearly can be used.

According to the treatment tool, the treatment tool can appropriately grip the target to be gripped by merely moving the driving manipulation member by the treatment tool in substantially one direction between the first position and the second position.

What is claimed is:

1. A treatment tool comprising:
an elongated shaft member having a distal end portion and a proximal end portion, and a longitudinal axis extending from the distal end portion to the proximal end portion;
a pair of grasping members installed at the distal end portion of the elongated shaft member so as to be freely opened and closed with each other to grasp a target area;
a driving force transmission member connected to the pair of grasping members and extending along the longitudinal axis so as to be freely moved along the longitudinal axis with respect to the elongated shaft member;
a driving manipulation member connected to a proximal end portion of the driving force transmission member and configured to be capable of being manipulated so that the driving force transmission member moves with respect to the elongated shaft member;
a switch unit having a first section and a second section in which the driving manipulation member is capable of sliding; and
a manipulation unit main body installed at tile proximal end portion of the elongated shaft member, wherein
the switch unit is configured to switch between a first state in which the driving manipulation member is rotated about a first rotational axis with respect to the manipulation unit main body and a second state in which the driving manipulation member is rotated about a second rotational axis different from the first rotational axis with respect to the manipulation unit main body, the first state being a state in which the driving manipulation member is slid in the first section, and the second state being a state in which the driving manipulation member is slid in the second section,
a ratio of a magnitude of a force for moving the driving force transmission member with respect to a magnitude of a force for sliding the driving manipulation member is a first ratio when the driving manipulation member is slid in the first section, and the ratio is a second ratio different from the first ratio when the driving manipulation member is slid in the second section.

2. The treatment tool according to claim 1, wherein
the switch unit allows the pair of grasping members to open and close and switches a ratio of a movement amount of the driving force transmission member with respect to a manipulation amount of the driving manipulation member with respect to the manipulation unit main body, in accordance with a manipulation amount of the driving manipulation member with respect to the manipulation unit main body.

3. The treatment tool according to claim 2, wherein
the driving manipulation member moves from a start position to an end position or from the end position to the start position in substantially one direction with respect to the manipulation unit main body,
the switch unit switches a rotational center of the driving manipulation member with respect to the manipulation unit main body from the first rotational center to the second rotational center or from the second rotational center to the first rotational center at at least one place between the start position and the end position, and
provided that a magnitude of a force applied to the driving manipulation member is set as $F_{in}$, a magnitude of a force for driving the driving force transmission member via the switch unit is set as $F_{out}$, a distance between an input section and the first rotational center when a predetermined point at which a force is applied to the driving manipulation member to manipulate the driving manipulation member is designated as the input section is set as $L_1$, a distance between a connecting position of the driving force transmission member to the driving manipulation member and the first rotational center is set as $L_2$, a distance between the input section and the second rotational center is set as $L_3$, and a distance between the connecting position and the second rotational center is set as $L_4$,
a relational expression in the first state is $F_{out}/F_{in}=L_1/L_2$,
a relational expression in the second state is $F_{out}/F_{in}=L_3/L_4$, and
a relational expression is $L_1/L_2<L_3/L_4$.

4. The treatment tool according to claim 1, wherein the first section and the second section are formed continuously with each other.

* * * * *